United States Patent [19]  [11]  4,345,591
Hedgren  [45]  Aug. 24, 1982

[54] MOUND DRESSING
[75] Inventor: Erland Hedgren, Täby, Sweden
[73] Assignee: Salve S.A., Switzerland
[21] Appl. No.: 239,141
[22] Filed: Feb. 27, 1981

Related U.S. Application Data

[63] Continuation of Ser. No. 940,087, Sep. 6, 1978, abandoned.

[51] Int. Cl.³ .............................................. A61F 13/00
[52] U.S. Cl. .................................... 128/169; 128/157
[58] Field of Search .............. 128/155, 156, 157, 169, 128/327, 325, 82, 132 D, 132

[56] References Cited

U.S. PATENT DOCUMENTS

| 2,453,705 | 11/1948 | Gallagher | 128/156 |
| 2,560,712 | 7/1951 | Bell | 128/156 |
| 2,934,066 | 4/1960 | Stowasser | 128/156 |
| 3,625,209 | 12/1971 | Clark | 128/169 |
| 4,005,709 | 2/1977 | Laerdal | 128/155 |

FOREIGN PATENT DOCUMENTS

| 640584 | 5/1962 | Canada | 128/156 |
| 603186 | 4/1926 | France | 128/156 |
| 2226188 | 11/1974 | France | 128/156 |
| 17544 | 7/1927 | Netherlands | 128/156 |

Primary Examiner—Henry J. Recla
Assistant Examiner—J. L. Kruter

[57] ABSTRACT

A wound dressing for use in first aid is described comprising a bandage to which is secured, by two parallel seams, a compress. The compress has flaps which can be folded over the region between the two seams, or which can be opened out. An open mouthed pocket is defined between the two seams which can accommodate a rigid body, such as a rolled bandage, to enable the wound dressing to be utilised to staunch a flow of blood. With the rolled bandage removed from the pocket and the flaps opened out, the wound dressing may be utilised to dress a large wound, such as a burn.

2 Claims, 1 Drawing Figure

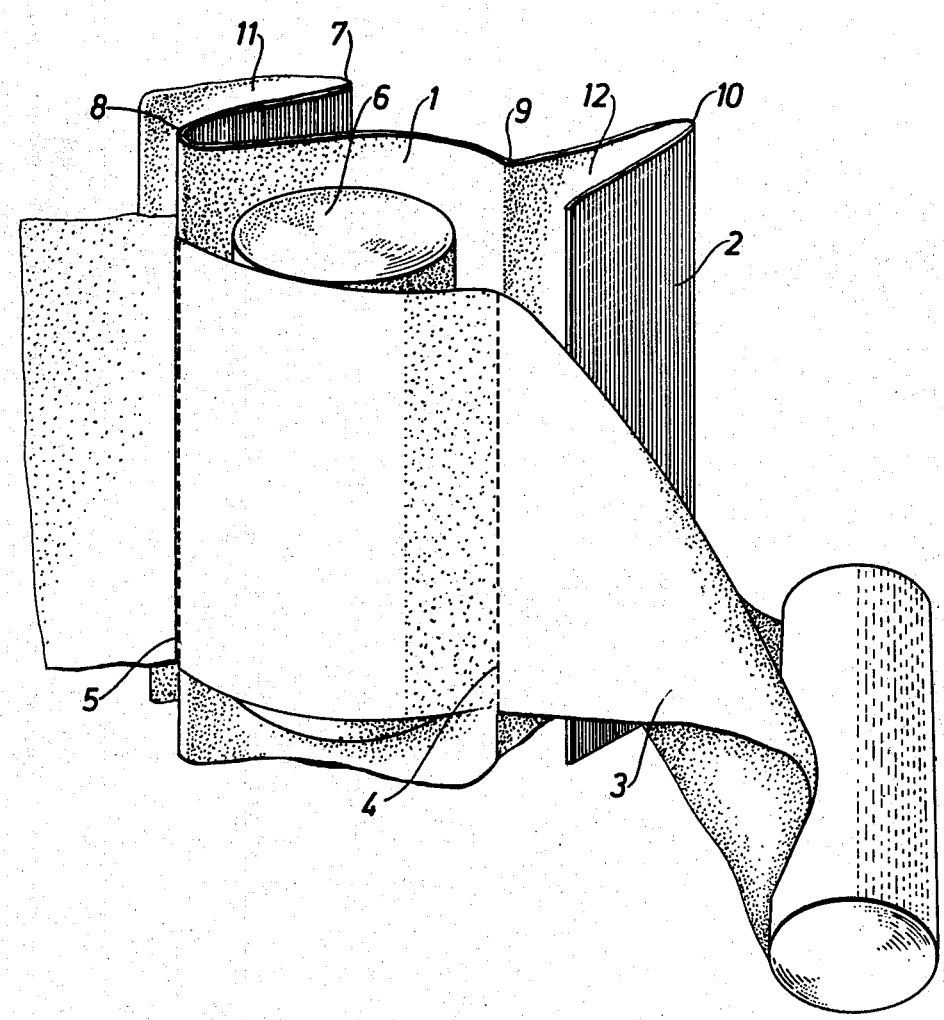

MOUND DRESSING

This is a continuation Application of Ser. No. 940,087, filed Sept. 6, 1978 and now abandoned.

BACKGROUND OF THE INVENTION

The present invention relates to a wound dressing and more particularly to a wound dressing comprising a bandage and suitable for use in first aid.

At the present time, many different types of wound dressing exist, and it is preferable to utilise one type of wound dressing where it is necessary to staunch a strong flow of blood and it is preferable to utilise another type of wound dressing where a large external wound has to be bandaged. Thus it is necessary, in any particular case, to select which type of wound dressing is to be utilised. This is a disadvantage, since in an emergency situation, the selection and obtaining of the correct wound dressing can cause an undesirable delay.

OBJECT OF THE INVENTION

It is one object of the present invention to provide a wound dressing which can be used in various ways.

It is another object of the invention to provide a wound dressing which can be utilised in conjunction with a rigid body, to staunch a flow of blood, or which can be utilised to dress a large external wound.

It is a further object of the invention to provide a wound dressing which will not adhere to a healing wound.

SUMMARY OF THE INVENTION

According to this invention there is provided a wound dressing comprising a bandage and a compress secured to the bandage, the compress being secured to the bandage at two spaced locations so that an open mouthed pocket is defined between the bandage and the compress. The compress may have flaps extending beyond regions of the compress between said two spaced locations to enable the compress to have one or two predetermined conditions, the first predetermined condition being one in which the compress has said flaps folded over the region between the two spaced locations, and the second predetermined condition being one in which the compress is spread out.

Conveniently the compress may be secured to the bandage by two spaced parallel seams which extend transversely across the bandage, and conveniently the compress may comprise a piece of material which extends beyond the two seams, the portions extending beyond the seams defining the flaps.

Advantageously, the length of bandage between the seams differs from, and is preferably greater than, the length of the compress between the two seams.

The compress may be provided with fold indications, such as creases, and the surface of the compress remote from the bandage may be treated, for example, metallized, to prevent a healing wound adhering to the surface of the compress.

The bandage and the compress may be of different transverse widths, the compress preferably being wider than the bandage.

When the wound dressing is to be utilised to staunch a flow of blood a rigid body, such as a rolled bandage, may be inserted into said pocket. The provision of the rigid body within the pocket may enable sufficient pressure to be obtained to stop the flow of blood, but if the wound dressing is not used to apply pressure to a wound, the rolled bandage contained within the pocket can be removed and can be used as additional bandage material. The flaps may be spread out when the wound dressing is used to dress a wound such as a burn.

Preferably, when the flaps and the compress are folded in, the compress can absorb large quantities of blood, for example if the wound dressing is being used as a pressure bandage.

BRIEF DESCRIPTION OF THE DRAWING

In order that the invention may be more readily understood and so that further features thereof may be appreciated, the invention will now be described with reference to the accompanying drawing, which is a perspective view of a wound dressing in accordance with the present invention.

FIGURE 1 is a perspective view of the bandage of the present invention.

DETAILED DESCRIPTION OF PREFERRED EMBODIMENT

Referring to the accompanying drawing a wound dressing in accordance with the present invention comprises an absorbent compress 1 which is in the form of a web or sheet of porous material, having a surface 2 which is intended to come into contact with a wound being dressed. This surface 2 of the compress is treated in such a way that the compress does not adhere to a wound whilst the wound is healing. For instance, the surface 2 of the compress 1 may be metallized.

The compress 1 is secured to a bandage 3, adjacent one end thereof, by means of two parallel stitched seams 4, 5, which extend transversely of the bandage 3. The length of the material in the bandage between the seams 4 and 5 is preferably greater than the length of the material in the compress between the seams 4 and 5. It will be appreciated that the seams 4 and 5 define an open-mouthed pocket, and this pocket is dimensioned to accommodate a substantially rigid body in the form of a rolled bandage 6. When such a body 6 is contained within the pocket the bandage can usefully be utilised to staunch a flow of blood, the rigid body being strongly urged into contact with the wound.

The compress 2 extends beyond the seams 4 and 5, and the regions of the compress which extend beyond the seams 4 and 5 define flaps 11 and 12. The compress 1 is provided with fold indications in the form of creases 7, 8, 9, 10 and when the compress is folded along the creases the flaps 11, 12 are folded to lie over the region of the compress 1 between the seams 4 and 5, and thus the compress effectively has fine thicknesses. This enables the entire absorption capacity of the compress 1 to be located over an appropriately dimensioned wound.

If a large wound, such as a burn, has to be treated, the flaps 11, 12 can be folded out initially by opening the fold creases 8 and 9 and, if necessary, by opening the fold creases 7 and 10. If the compress is opened at all four fold creases, the compress may be applied to a wound as a single layer.

It is envisaged that the compress would be treated appropriately so that the compress is sterile, the wound dressing thus being supplied in the form of a sterile dressing. It is envisaged that the rolled bandage 6 would be located within the pocket when the wound dressing is supplied.

When the wound dressing is to be utilised the person utilising the wound dressing may easily decide whether the rolled bandage 6 is to be left within the pocket or is to be removed from the pocket depending upon the precise nature of the wound to be treated. Also the person utilising the bandage will readily be able to assess whether the flaps 11, 12 are to be left in an initial folded in condition, are to be folded out, merely by assessing the size of the wound to be dressed.

It will be appreciated that the wound dressing described above will be ready for instant use, and it is not necessary to take any special steps to prepare the wound dressing for use. Thus, only a minimum amount of time is utilised in applying the wound dressing to a wound. It will also be appreciated that an advantage of the wound dressing described above is that the specially treated surface is applied to the wound, thus reducing the risk of the wound adhering to the dressing during the healing process.

It is to be appreciated that the invention is not limited to the specific embodiment illustrated in the accompanying drawing and described above, as many modifications are possible within the scope of the invention. For example, the length of the material in the bandage and in the compress between the seams may be the same, and it is conceivable that this would be an advantage during manufacture. The compress and the bandage can have any appropriate width but it is to be understood that in most cases it will probably be preferable for the compress to be wider than the bandage. Also it is to be appreciated that the surface of the compress which is intended to come into contact with the wound may be treated in any appropriate manner to minimise the risk of the compress adhering to the wound. Furthermore, whilst an embodiment has been described in which the flaps on either side of the seams can be folded double across the region of the compress between the seams, the flaps may be made of greater length and may be folded to have many thicknesses above the region of the compress between the two seams.

What is claimed is:

1. A wound dressing comprising an elongated rolled bandage having longitudinal edges and an elongated sheet compress laid lengthwise one overlying the other, said compress having a width larger than the width of the bandage and being stitched to the bandage forming two spaced seams extending transversely across the width of the bandage, the length of bandage between said two spaced seams being greater than the length of the compress between said two spaced seams to define a normally open pocket between the bandage and the compress which is open along the respective longitudinal edges for the removable insertion of an additional bandage means therebetween, said compress having a pair of flaps respectively extending freely beyond said two spaced seams to enable the compress to have one of two predetermined conditions, the first predetermined condition being one in which said flaps are folded over the region between the two spaced seams and the second predetermined condition being one in which said flaps are spread along a substantial portion of the length of the bandage, said compress being adapted to be applied against a wound on the body of a living subject and said bandage, adapted to be applied to the body, acting to pull the portion of said compress between said seams taut thereby applying pressure to said wound.

2. The dressing according to claim 1 wherein said additional bandage means comprises a substantially rigid rolled bandage located in said pocket, said rolled bandage being of a size to coact with said bandage when pulled to apply pressure on said compress and wound.

* * * * *